United States Patent
Eden et al.

(10) Patent No.: US 6,815,891 B2
(45) Date of Patent: Nov. 9, 2004

(54) METHOD AND APPARATUS FOR EXCITING A MICRODISCHARGE

(75) Inventors: J. Gary Eden, Mahomet, IL (US); Sung-Jin Park, Yong-In (KR); Clark J. Wagner, Urbana, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 109 days.

(21) Appl. No.: 10/062,269

(22) Filed: Oct. 26, 2001

(65) Prior Publication Data

US 2003/0080664 A1 May 1, 2003

(51) Int. Cl.[7] .................................................. H01J 17/04
(52) U.S. Cl. ........................ 313/618; 313/356; 313/631
(58) Field of Search ................................ 313/356, 618, 313/631, 632, 498, 567, 574; 257/12, 656; 372/87; 438/20

(56) References Cited

U.S. PATENT DOCUMENTS

| | | | | |
|---|---|---|---|---|
| 4,110,775 A | * | 8/1978 | Festa | 257/484 |
| 4,672,624 A | * | 6/1987 | Ford | 372/87 |
| 5,013,902 A | * | 5/1991 | Allard | 250/214 VT |
| 5,055,979 A | * | 10/1991 | Boland et al. | 362/558 |
| 5,062,116 A | * | 10/1991 | Christensen | 372/61 |
| 5,200,973 A | * | 4/1993 | Ford | 372/87 |
| 5,387,805 A | * | 2/1995 | Metzler et al. | 257/147 |
| 5,686,789 A | | 11/1997 | Schoenbach et al. | |
| 5,939,829 A | | 8/1999 | Schoenbach et al. | |
| 6,016,027 A | | 1/2000 | DeTemple et al. | |
| 6,082,294 A | | 7/2000 | Simpson | |
| 6,139,384 A | | 10/2000 | DeTemple et al. | |
| 6,353,289 B1 | * | 3/2002 | Ishigami et al. | 313/637 |
| 6,563,257 B2 | * | 5/2003 | Vojak et al. | 313/356 |

FOREIGN PATENT DOCUMENTS

JP          7192701          7/1995

OTHER PUBLICATIONS

"High–Pressure Hollow Cathode Discharges;" Karl H. Schoenbach et al.; Physical Electronics Research Institute, Old Dominion University, Norfolk, VA, USA; Jun. 30, 1997.
"Microdischarge Devices Fabricated in Silicon;" J.W. Frame et al.; Department of Electrical and Computer Engineering, Everett Laboratory, University of Illinois, Urbana, Illinois, USA; Jun. 30, 1997; App. Phys. Lett. 71 (9), Sep. 1, 1997.
"Flexible Microdischarge Arrays: Metal/Polymer Devices;" S.–J. Park et al.; Laboratory for Optical Physics and Engineering, Department of Electrical and Computer Engineering, University of Illinois, Urbana, Illinois, USA; May 17, 2000; Applied Physics Letters, vol. 77, No. 2, Jul. 10, 2000.
"Emission of Excimer Radiation from Direct Current, High–Pressure Hollow Cathode Discharges;" Ahmed El–Habachi and Karl H. Schoenbach; Electrical and Computer Engineering Department, Physical Electronics Research Institute, Old Dominion University, Norfolk, Virginia, USA; Nov. 4, 1997; App. Phys. Lett. 72 (1), Jan. 5, 1998.

* cited by examiner

Primary Examiner—Vip Patel
Assistant Examiner—Karabi Guharay
(74) Attorney, Agent, or Firm—Brinks Hofer Gilson & Lione

(57) ABSTRACT

A discharge device has a diode with a depletion region, a channel extending through a surface of the diode, and a gas within the channel. The gas is excited and a discharge formed by reverse biasing the diode and establishing an electric field in the depletion region of the diode.

50 Claims, 7 Drawing Sheets

METHOD AND APPARATUS FOR EXCITING A MICRODISCHARGE

FEDERALLY SPONSORED RESEARCH AND OR DEVELOPMENT

This invention was made with Government support under Contract No. F49620-98-1-0030 awarded by the U.S. Air Force Office of Scientific Research (AFOSR). The Government has certain rights in the invention.

BACKGROUND

The present invention relates to microdischarge devices and, in particular, to novel structures for light emitting devices and low-cost methods of producing ultraviolet or visible light.

It has long been known that electrical discharges are efficient sources of light and, today, gas discharge lamps (including fluorescent sources, and metal-halide, sodium, or mercury arc lamps) account for most of the world's light-generating capacity (several billion watts on a continuous basis). Most of these devices are, unfortunately, bulky and frequently have fragile quartz or glass envelopes and require expensive mounting fixtures. In addition to general lighting, discharges produce ultraviolet and visible light for other purposes such as germicidal applications (disinfecting surfaces and tissue), cleaning electronic and optical surfaces in manufacturing, and activating light-sensitive molecules for medical treatments and diagnostics.

Although microdischarges were demonstrated by A. D. White in 1959, only recently were microdischarge devices fabricated in silicon by techniques developed in the integrated-circuit industry. As shown in FIG. 1, a microdischarge device 100 fabricated in silicon had a cylindrical channel (microcavity) 102 in the cathode 104 of the device 100. The semiconductor cathode 104 was affixed to a copper heat sink with conductive epoxy. The anode 106 for the microdischarge device 100 was typically a metal film such as Ni/Cr. A thin dielectric layer 108 deposited onto the silicon electrically insulates the cathode 104 from the anode 106. When the channel 102 is filled with the desired gas and the appropriate voltage imposed between the cathode 104 from the anode 106, a discharge is ignited in the channel 102.

Microdischarges have several distinct advantages over conventional discharges. Since the diameter of single cylindrical microdischarge devices, for example, is typically less than 400–500 $\mu$m, each device offers the spatial resolution that is desirable for a pixel in a display. Also, the small physical dimensions of microdischarges allows them to operate at pressures much higher than those accessible to conventional, macroscopic discharges. When the diameter of a cylindrical microdischarge device is, for example, on the order of 200–300 $\mu$m or less, the device will operate at pressures as high as atmospheric pressure and beyond. In contrast, standard fluorescent lamps, for example, operate at pressures typically less than 1% of atmospheric pressure.

Despite their applications in several areas, including opto-electronics and sensors, microdischarge devices have several drawbacks. For example, extracting optical power from deep cylindrical cavities is frequently inefficient. If the cylindrical cathode for a microdischarge is too deep, it will be difficult for photons produced below the surface of the cathode to escape. Furthermore, the conventional microdischarge devices require an insulating/dielectric layer fabricated from a material different from that of than either the anode or cathode. The presence of this layer complicates fabrication of the device. For example, $SiO_2$ films, polymers, glass, quartz and mica have been used as the insulating layer. However, in such a three-layer microdischarge device, drilling the top layer with a laser is straightforward, but ablating the $SiO_2$ layer is not, and results in a cylindrical channel that is often not clean. The device quality thus is deteriorated.

BRIEF SUMMARY

In view of the above, novel microdischarge devices and fabrication methods are provided.

In one embodiment of the invention, the discharge device comprises a diode with a channel that extends through the surface of at least one of the first and second layers of the diode. A gas is disposed within the channel.

The diode may be a p-n diode, p-i-n diode, or Schottky diode. In addition, a dielectric layer and an electrode may be formed on the diode and may be biased independently of the diode. The dielectric layer may be formed from a plurality of films with at least one of the films having a dielectric constant different from at least one other of the films. A conducting screen may be disposed on at least one end of the channel. Similarly, an optically transmissive sealing material, which does not substantially absorb light of a wavelength emitted by the gas when the gas is electrically excited, may be used to seal the channel. An optically transmissive protective surface to protect the surface of the sealing material may be disposed between the sealing material and the surface of the diode.

An annular chamfer that widens the channel may be introduced to permit coupling of the discharge to an optical fiber. A bias resistor may be connected in series with the diode to regulate light output of the device.

A plurality of devices may be arranged in an array. The array may be divided into independently excited sub-arrays. The sub-arrays may have at most one of the voltages, applied to the first and second layers, in common.

In another embodiment of the invention, a method of fabricating a discharge device comprises forming a channel extending from a surface of the diode at least through a depletion region of the diode and introducing a gas to the channel.

The method may further comprise exciting the gas to form a discharge by reverse biasing the diode. In addition, the method may further comprise selecting the gas, determining an optimum reverse breakdown voltage for excitation of the gas, and selecting material of the diode prior to forming the channel.

Further, the method may comprise extending the depletion region through an intermediate semiconductor layer of the diode having a lower electrical conductivity than layers that establish the depletion region or biasing a dielectric layer and an electrode layer formed on the surface of the diode independently from the diode. The method may additionally comprise forming an annular chamfer that widens the channel and further coupling an optical fiber to the annular chamfer.

The method may comprise altering the electric field present in the channel by affixing a conducting screen to at least one end of the channel and additionally coating the screen with a phosphor or electroluminescent material. The method may also comprise sealing the channel with an optically transmissive sealing material that does not substantially absorb light of a wavelength emitted by the gas when the gas discharges.

The method may comprise arranging a plurality of the devices in an array and further dividing the array into independently excited sub-arrays.

The following figures and detailed description of the preferred embodiments will more clearly demonstrate these and other advantages of the invention.

DETAILED DESCRIPTION

The present invention provides microdischarge devices and arrays of microdischarge devices that are fabricated using either p-n or Schottky diodes. The diodes are reverse biased and gas in the diodes ignite in the depletion region, where the majority of the electric field resides. As a result, the present devices are inexpensive to manufacture and have superior electrical and optical characteristics to those of previous microdischarge devices. The present microdischarge devices and arrays may operate at atmospheric pressure and at voltages of 120V or less. Either DC or AC voltages may be applied to produce the discharge.

Figure 1:
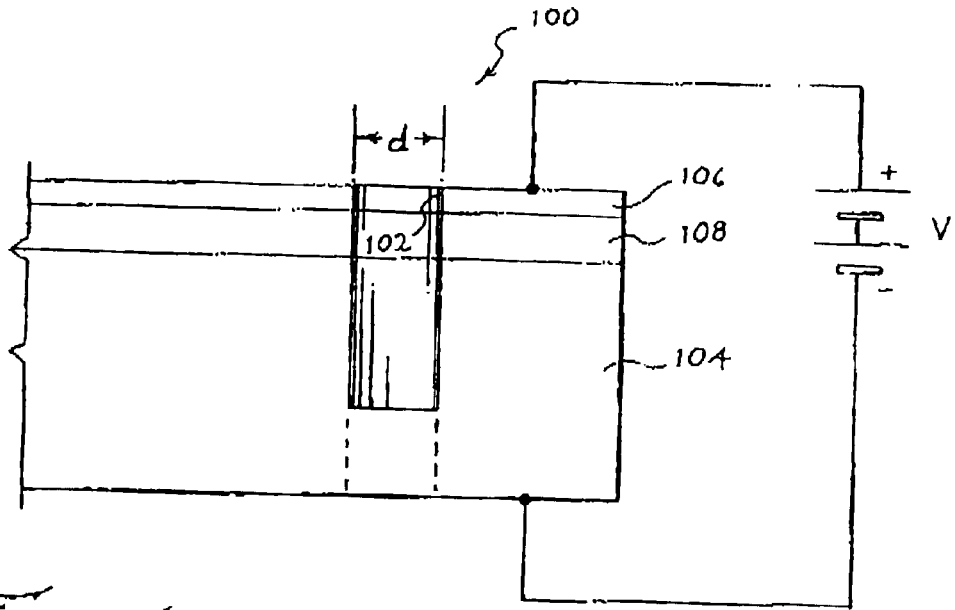
FIG. 1 is a cross-sectional view of a conventional microdischarge device.
Figure 2:
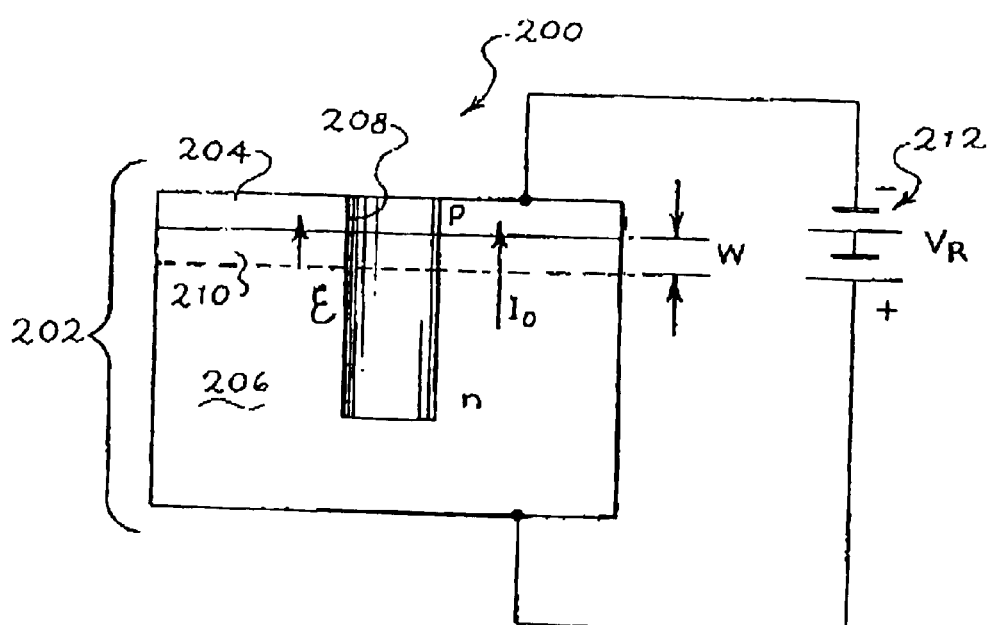
FIG. 2 is a cross-sectional view of an embodiment of the microdischarge device of the present invention.

A first embodiment of a microdischarge device (not drawn to scale) is shown in FIG. 2. The microdischarge device 200 is formed from a diode 202. The diode 202 has a p-type semiconductor layer 204 and an n-type semiconductor layer 206. A channel 208 is formed through the depletion region 210 of the diode 202 and the surface of at least one of the semiconductor layers 204 and 206. Thus, although in FIG. 2, the channel 208 is shown as being formed solely from the surface of the p-type layer 204 through the depletion region 210 and terminating in the n-type semiconductor layer 206, the channel 208 may be formed through the entirety of both layers 204 and 206.

A diode has device characteristics such that application of a voltage that forward biases the diode (say 1 V) exhibits a superlinear change in current from the application of a voltage having the same magnitude but opposite sign (i.e. −1 V) that reverse biases the diode. Prior microdischarge devices using dielectric layers do not exhibit such superlinear changes in corresponding voltage ranges, for example from 1 V to −1 V, as the dielectric material exhibits a large resistance with an applied voltage of either sign. In general, forward biased diodes exhibit an exponential increase in current with increasing forward bias. Resistances of the diode in the forward active region of operation are usually negligible compared with connected external resistances. Under reverse bias, the increase of current with increasing reverse bias voltage is generally extremely small, typically being essentially constant, until breakdown of the diode is reached. Note that, however, the breakdown of diodes varies widely with the type of diode: the breakdown of Zener diodes, for example may occur at a reverse bias of only a few volts while that of other diodes may be hundreds of volts. In addition, the diode may be part of a bipolar junction transistor (BJT) or semiconductor controlled rectifier (SCR), both of which comprise at least two p-n semiconductor diodes, or a field effect transistor (FET), which comprises two metal-semiconductor junction diodes.

The semiconductor layers are both electrically and thermally conductive. Preferably, the semiconductor layers have a resistivity of not less than 10 Ω-cm, more preferably not less than 25 Ω-cm or 50 Ω-cm. A reverse bias, forming an electric field in excess of the built-in electric field, is established across the depletion region 210 by a voltage source 212 connected between the p-type semiconductor layer 204 and the n-type semiconductor layer 206. Ohmic contacts to the p-type and n-type layers that permit an external voltage to be applied to the layers are not shown. The potential difference across the depletion region 210 creates a discharge in the channel 208 when a gas is present in the channel 208. The resulting light has emission spectra that are characteristic of the gas or gas mixture selected. This light is subsequently emitted from at least one end of the channel 208.

The p-type and n-type semiconductor layers are planar. The layers may be fabricated on a substrate or, as shown in FIG. 2, may be fabricated from a substrate in any of the numerous conventional manners in which a diode may be formed, e.g. diffusion or deposition. Although FIG. 2 and the other figures show the diode 202 as an n-type substrate with a p-type layer, the diode may also be a p-type substrate with an n-type layer. The doping of the semiconductor layers is determined according to the device design; for example, at least one side of the diode 202 may be heavily doped, in excess of about $10^{18}$ cm$^{-3}$, to increase the electric field in the depletion region 210 and/or to allow better contact between the side and the voltage source 212. Preferably, the upper layer has a thickness of less than 100 μm, more preferably a thickness from about 10 Å –10 μm or from 50 Å –5 μm.

The p-type and n-type semiconductor layers may be an optically transmissive material that does not substantially absorb light of a selected wavelength emitted by the gas when the gas is excited (for example, electrically excited). Optically transmissive material transmits preferably at least 50% of light impinging substantially normal to the surface of the material at wavelength of the discharge. More preferably, optically transmissive material transmits at least 60%, 70%, 80%, 90%, or 95% of light impinging substantially normal to the surface of the material at wavelength of the discharge. One example of such a semiconductor layer is silicon carbide (SiC), which is highly transmissive to visible light.

The p-type and n-type layers are connected to the voltage source 212. The types of materials and methods to make ohmic contact to the p-type and n-type layers 204 and 206 are well-known in the art of semiconductor device fabrication.

The channel 208 preferably has a substantially cylindrical shape. This makes it easier to couple to optical fiber, for example. Other shapes are also possible, depending on the material system or processing used. The channel is formed in a direction transverse to the semiconductor layers and preferably has a diameter of 0.1 $\mu$m–1 mm. More preferably, the diameter ranges from 0.1 $\mu$m–500 $\mu$m, 1 $\mu$m–100 $\mu$m, or 100 $\mu$m–500 $\mu$m. The channel is filled with a gas selected for its breakdown voltage or light emission properties at breakdown. Light is produced when the voltage difference between the p-type and n-type layer creates an electric field in the depletion region 210 sufficiently large to electrically break down the gas (nominally about $10^4$ V/cm). This light escapes from the channel 208 through at least one end of the channel 208.

The gas that fills the channel 208 may be selected for its light emission properties at breakdown. The term gas herein refers to acceptable single gases, gas mixtures, and vapors. Examples of gases are the rare gases (He, Ne, Ar, Xe, and Kr), and $N_2$. In addition, a wide variety of gas mixtures exist that, when excited, also produce intense emission from atomic or molecular species. An example of the former is Ar/Hg vapor and the latter includes rare gas/halogen donor gas mixtures (such as one or more rare gases mixed with $F_2$, $NF_3$, $XeF_2$, $N_2F_4$, HCl, $Cl_2$, $I_2$, HI or other halogen-bearing molecules). Another example is the XeO (xenon oxide) excimer that is produced in mixtures of Xe and $O_2$, $N_2O$ or $NO_2$ gases. Such gases, however, need not be present in the channel: breakdown may occur when air is present.

It is well known that the width of the depletion region 210 varies with the reverse bias voltage, $V_R$, of the diode 200, specifically W is proportional to $VR_R^{1/2}$ where $V_R$ is the magnitude of the reverse bias applied to the diode. In addition, the reverse bias current, $I_0$, is essentially independent of $V_R$ until breakdown is reached. The introduction of the channel 208 allows a discharge to be produced in the gas intentionally introduced into the channel 208. This is possible as a majority of the reverse bias applied to the diode 200 appears across the depletion region 210, thereby increasing the electric field strength proportionally.

As the reverse bias current $I_0$ is essentially insensitive to the reverse bias voltage, varying the reverse bias voltage impacts primarily on the microdischarge. Increasing the reverse bias voltage increases the depletion width and thus decreases the junction capacitance. Thus, for a selected gas or mixture of gases, the properties of the p-n junction (e.g. the reverse breakdown voltage, doping levels in the semiconductor layers) can be designed and the optimum value of the reverse breakdown voltage determined for excitation of the gas. The reverse breakdown voltage, in turn, dictates the maximum electric field in the channel.

One of the advantages of this device is the ability to effect simultaneous control over both the shunt capacitance of the reverse biased p-n junction and the discharge E/N ratio. The discharge E/N ratio is the ratio of the electric field strength in the channel and the atomic or molecular number density of the gas. The reason for this is that the above ratio is proportional to $V_R^{1/2}$, while the capacitance is inversely proportional to the depletion width, i.e. $V_R^{-1/2}$, and thus the product of the two is approximately constant. This allows for a greater design flexibility for radio-frequency (RF) modulation of both individual microdischarge devices and arrays of devices. That is, to excite a microdischarge at radio frequencies, for example, one can match the shunt capacitance of the reverse-biased junction, $C_j$, with an external inductor to resonantly drive the microdischarge at the desired frequency.

Another advantage is that the entire device may be fabricated from Si, or any other structure capable of forming a depletion region. Other, non-exclusive examples of such a structure include homojunctions of elemental semiconductors such as Ge, compound semiconductors (including III–V and II–VI) such as SiGe, GaAs, GaN, semiconducting polymers, or heterojunctions of Si/Ge, GaAs/AlGaAs, InP/InGaAs, for example. This makes the fabrication of the device simple and inexpensive. For example, entire Si wafers having a p-n junction parallel to their surfaces are produced by well-known processes, such as diffusion. The replacement of the conventional dielectric layer with the depletion region reduces the cost significantly and simplifies the production of the devices as the channel is fabricated through only one type of material. The channel may be formed by mechanical or ultrasonic drilling, optical drilling (preferably by a pulsed laser), dry etching or wet chemically etching of the layers. These techniques are all well developed in the semiconductor industry.

Figure 3:
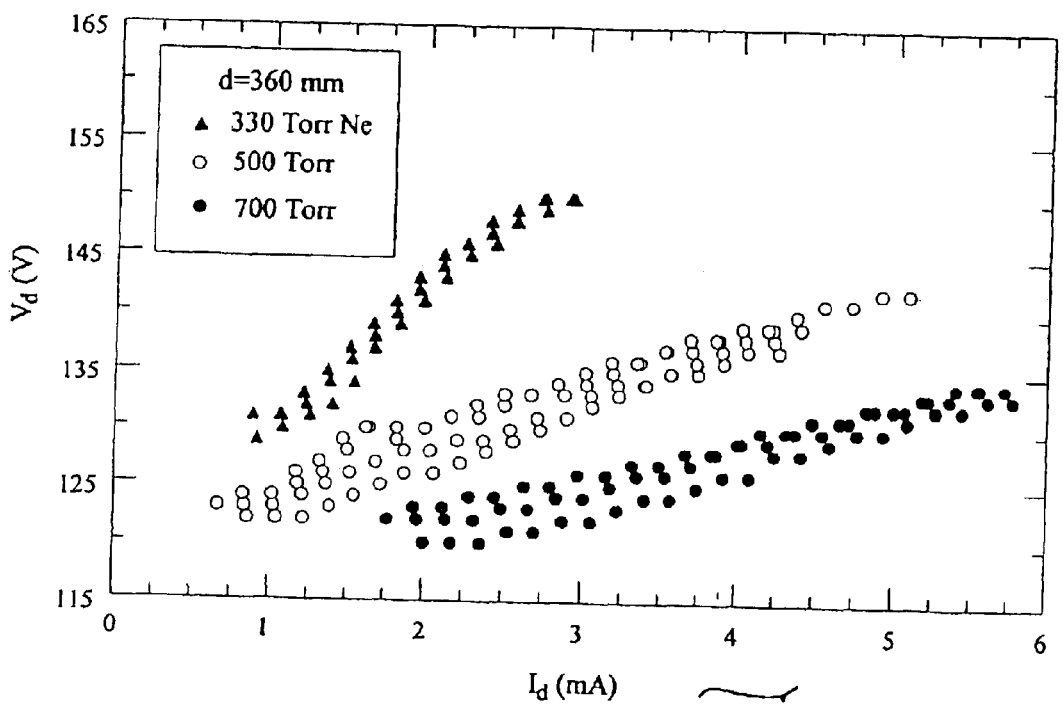
FIG. 3 illustrates V-I characteristics for several different Ne gas pressures in an embodiment of the microdischarge device of the present invention.
Figure 4:
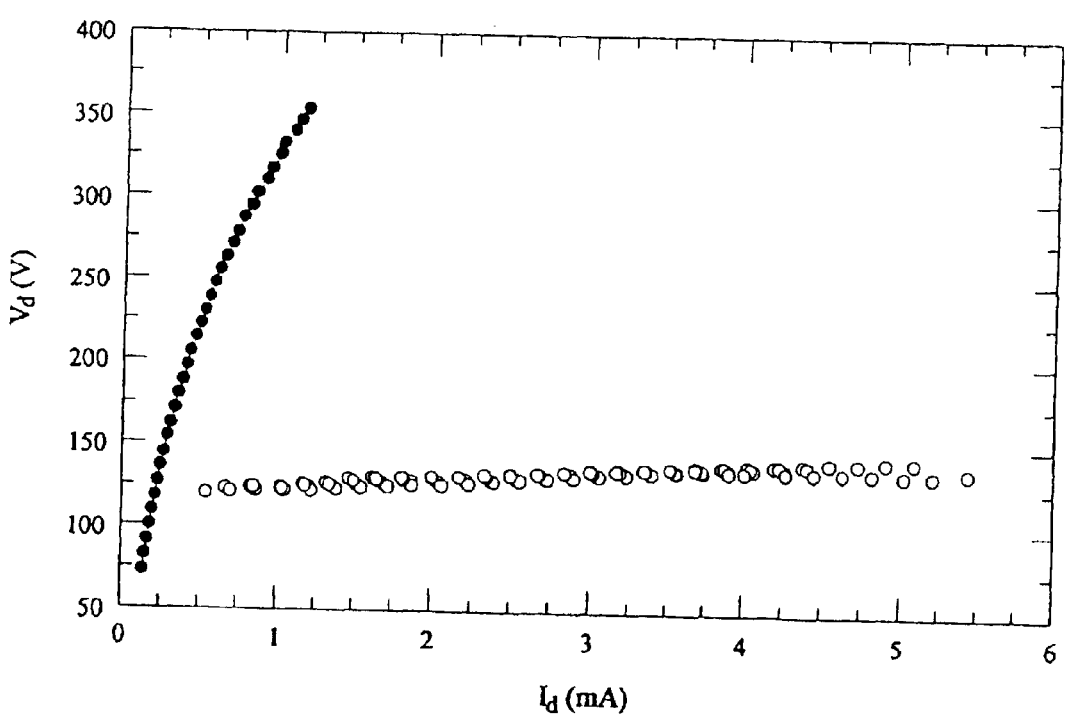
FIG. 4 illustrates V-I characteristics for an embodiment of the microdischarge device of the present invention.

FIGS. 3 and 4 are V-I data for a 360 $\mu$m diameter p-n device having a reverse breakdown voltage of 400 V. In FIG. 4, the V-I characteristics of a device operating prior to discharge and after ignition of the discharge using Ne gas at a pressure of 500 Torr and 55.2 K$\Omega$ of ballast. Prior to breakdown of the gas, the current rises slowly with increasing reverse bias voltage applied to the p-n junction as the voltage is changed from about 120 V to about 350 V. At about 350V of reverse bias, the gas ignites (a discharge is formed) and the device operating voltage falls to about 136 V and the current rises to about 5.4 mA.

The V-I characteristics for several different Ne gas pressures are presented in FIG. 3. Stable glow discharges are produced by devices at all of the pressures shown in the range, 200–700 Torr. The positive differential resistances of the devices are about 14, 4, and 3.5 k$\Omega$ at 330, 500, and 700 Torr, respectively. Thus, the devices may be operated without external ballast and work well at atmospheric pressures. The discharge operating voltage also decreases with increasing gas pressure. As an example, an operating voltage of about 120 V is obtained for an operating current and pressure of about 2 mA and 700 Torr, respectively.

Figure 5:
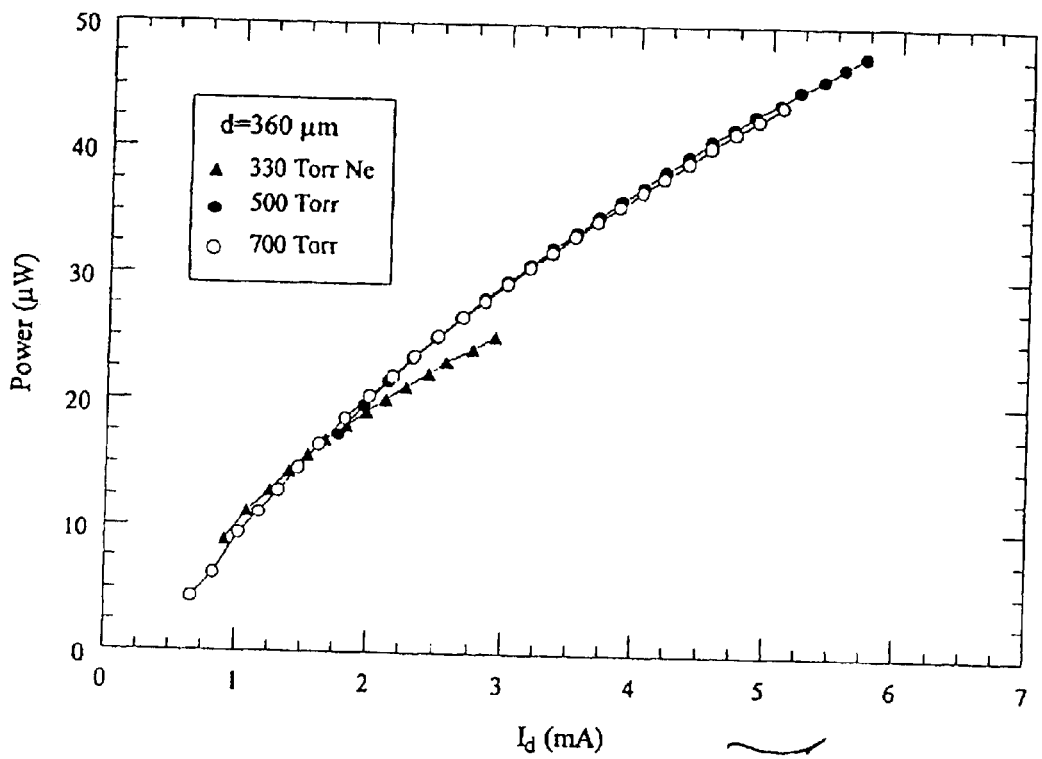
FIG. 5 illustrates emission intensity over the 300–800 nm spectral range for an embodiment of the microdischarge device of the present invention.

The emission intensity (or output power) of these devices over the 300–800 nm wavelength range is shown in FIG. 5. These measurements were taken over a solid angle of $5 \cdot 10^{-2}$ steradians and show output powers approaching 50 $\mu$W/device. As illustrated, the output powers are relatively insensitive to the gas pressure within the 300–700 Torr range. For these devices, a maximum output power of 48 $\mu$W was recorded for an operating current of 5.7 mA when the gas pressure was 700 Torr. However, optimal conversion of power dissipated in the discharge into radiative output occurs at lower values of current.

Figure 6:
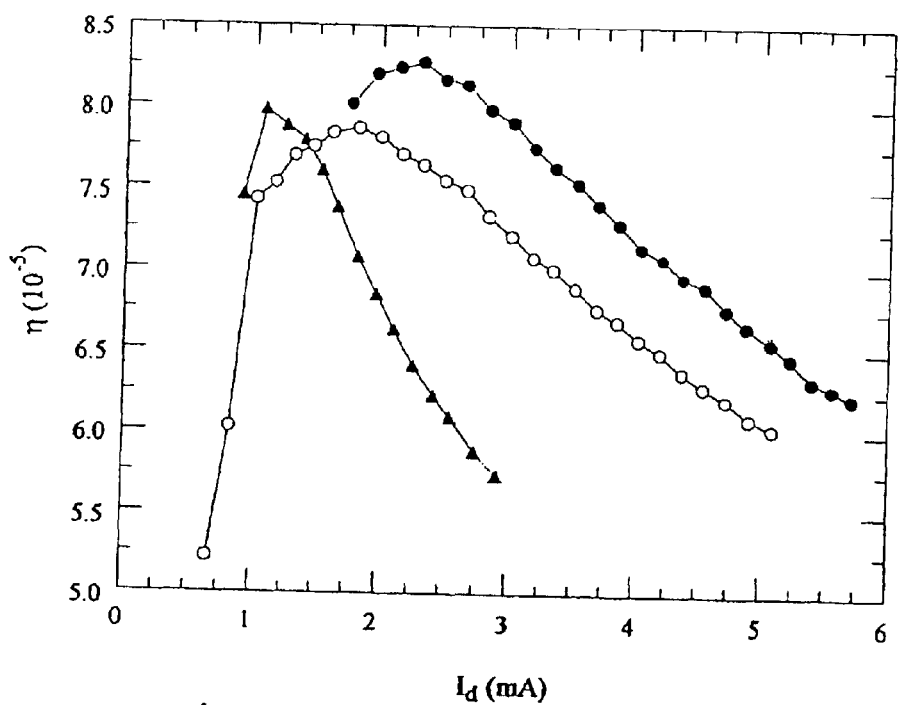
FIG. 6 illustrates efficiency as a function of applied current for an embodiment of the microdischarge device of the present invention.

Similarly, the efficiency of the devices is shown in FIG. 6. The measured peak efficiency of the Ne-filled devices exceeds $8 \times 10^{-5}$ measured over a small angle of about $6 \cdot 10^{-2}$ steradians. The discharge current at which the peak efficiency is reached increases with gas pressure. Thus, considerably higher radiative output levels are realized using more efficient molecular species such as excimers (e.g. rare gas halides or dimers) or Ar—$N_2$ rather than using less efficient atomic rare gases. Emission spectra of the microdischarges indicate that they behave as hollow cathodes for Ne pressures in excess of 150 Torr for the cylindrical channel diameter above. The intense discharge produced from a single 300 μm device operating at a Ne pressure of 200 Torr is readily visible across a well-lit room. The emission is azimuthally uniform and no noticeable degradation of the device surface is observed after several hours of operation.

While the above embodiment is directed towards a p-n junction diode, similar results may be obtained using a Schottky diode. The Schottky diode has a metal layer disposed on a semiconductor layer. For an n-type semiconductor layer, the work function for the semiconductor is smaller than the work function for the metal. For a p-type semiconductor layer, the work function for the semiconductor is larger than the work function for the metal. Any conventional metal may be used that forms a depletion region on the base semiconductor layer when the proper bias voltage is applied. Examples of Schottky diodes include Al on n-type Si.

Figure 7:
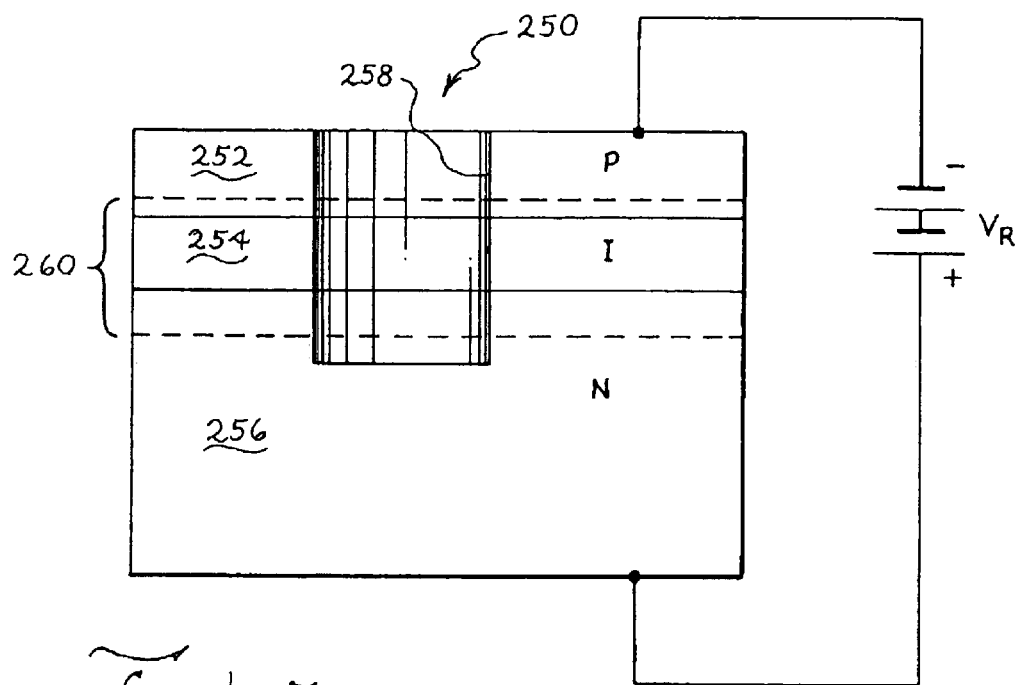
FIG. 7 is a cross-sectional view of an embodiment of the microdischarge device of the present invention.

In another embodiment, an intermediate semiconductor layer may be formed between the p-type and n-type semiconductor layers. The intermediate layer has a lower conductivity than the surrounding p-type and n-type semiconductor layers and may be an intrinsic, compensated, or lower doped semiconductor layer. One example of this, as shown in FIG. 7, is the p-i-n diode 250. The p-i-n diode 250 includes a p-type layer 252, an n-type substrate 256, and a channel 258. In addition, the p-i-n diode 250 has an intrinsic semiconductor layer 254 disposed between the p-type layer 252 and n-type substrate 256. The depletion region 260 extends through the intrinsic semiconductor layer 254, as well as into the p-type layer 252 and n-type substrate 256. An intrinsic semiconductor layer may be doped several orders of magnitude less than either the p-type layer or n-type substrate.

In another embodiment (not shown), a bias resistor is connected in series with the diode. The bias resistor is added to minimize the effect of photons generated in the channel having sufficient energy to be absorbed in the reverse-biased junction (i.e. larger than the bandgap energy), thereby increasing the reverse bias current. The bias resistor thus regulates the light output of the device.

Figure 8:
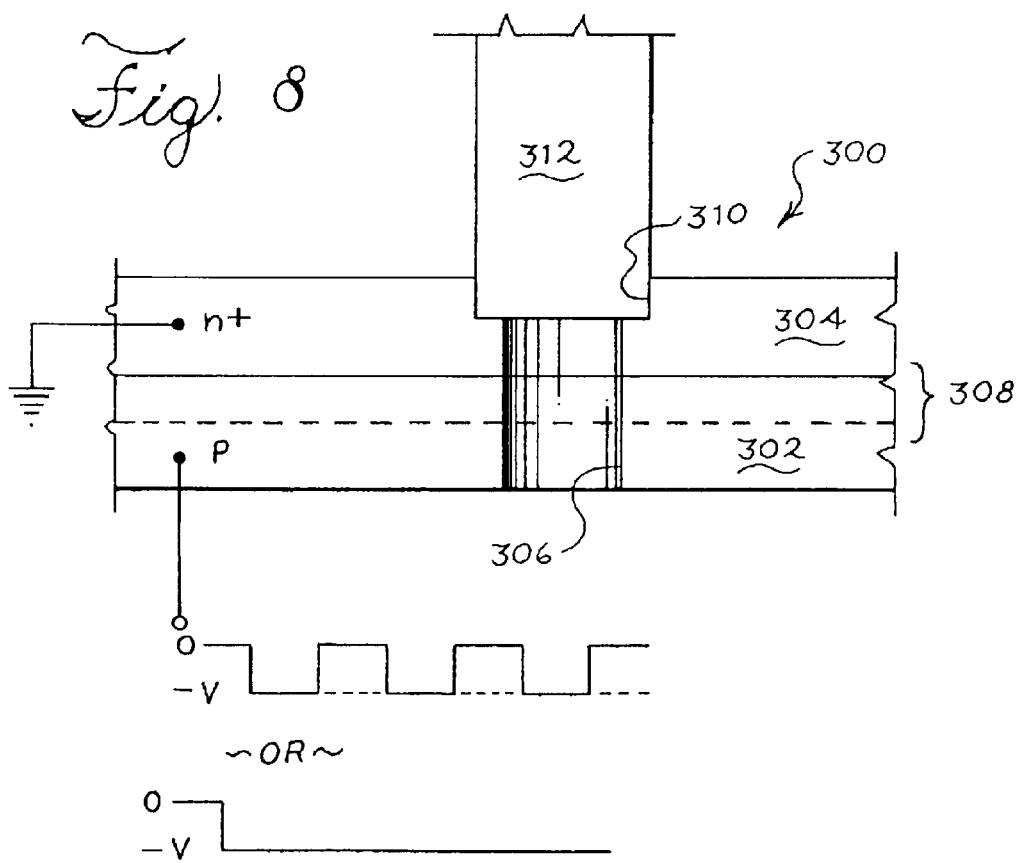
FIG. 8 is a cross-sectional view of an embodiment of the microdischarge device of the present invention.

FIG. 8 shows an embodiment in which the microdischarge device 300 is coupled with an optical fiber 312. In this device 300, the channel 306 is formed in the depletion region 308, p-type semiconductor layer 302 and n-type semiconductor layer 304 as above. However, in this case, an annular chamfer 310 is formed at the surface of the p-type semiconductor layer 302. The annular chamfer 310 widens the channel 306 such that the optical fiber 312 is accommodated therein. Note that in this embodiment, as others, the top layer (in this case the p-type semiconductor layer 302) may be grounded while a pulsed or CW voltage is applied to the lower layer. This configuration allows for efficient optical coupling of the discharge into the fiber 312 because the fiber core diameter can be selected to be equal to or greater than that of the channel 306. The fiber 312, in turn, may be any conventional fiber, such as an appropriately doped fiber that serves as a fluorescence converter. One example of such a fiber is a Ho:ZBLAN fiber, which converts red light from a Ne microdischarge into green light. An example of an application using the coupled fibers is a fiber bundle used to transport radiation from an array of devices (as described below) to another location in which one fiber is used per device.

Figure 9A:
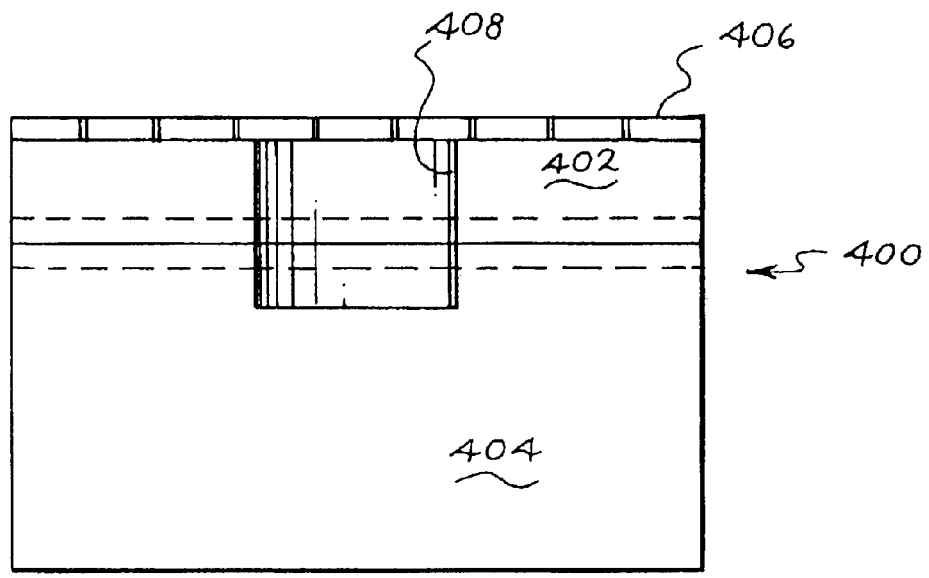
FIGS. 9a and 9b illustrate cross-sectional and top views of an embodiment of the microdischarge device of the present invention.
Figure 9B:
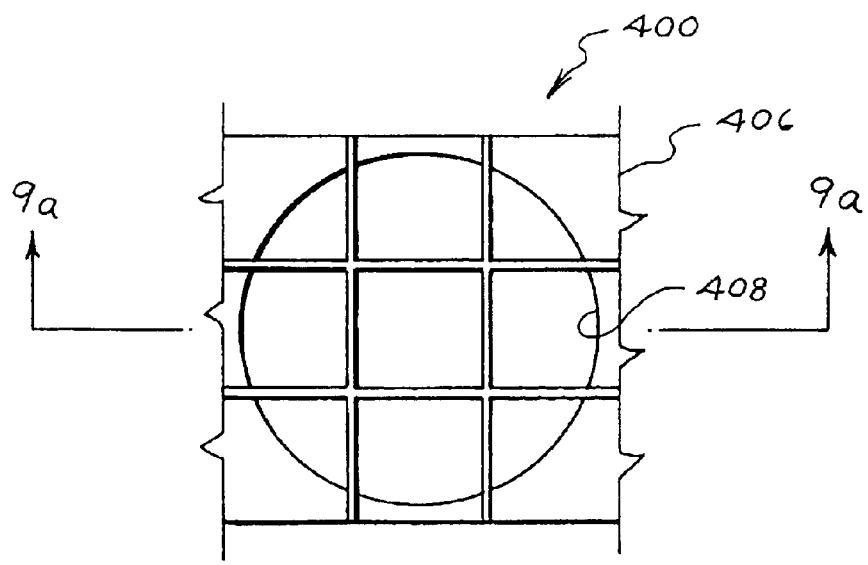

In another embodiment, shown in FIG. 9a, the microdischarge device 400 includes a conducting screen electrode (or screen) 406 that is in contact with and extends across at least one of the p-type semiconductor layer 402 or the n-type semiconductor layer 404. The screen 406 improves both the lifetime and light output of the microdischarge device 400, making it more efficient by allowing the device to operate at lower voltages and producing greater light output power at the same power. The screen 406, as shown in FIG. 9b, preferably has openings that are comparable to or smaller than the diameter of the channel 408.

The screen 406 may be mounted onto either (or both) the p-type semiconductor layer 402 or n-type semiconductor layer 404. The screen 406 presents a more uniform electrostatic potential to the discharge in the channel 408 as the screen partially covers the hole in the layer. The result of this is that the emission intensity of the discharge from the end of the channel 408 of microdischarge devices 400 in which the screen 406 is present is up to, for example, an order of magnitude larger than the emission intensity when a screen 406 is not present.

Preferably, screens are constructed of a metal such as Ni, Au, or Cu, which are available commercially as sample holders for Transmission Electron Microscopy (TEM) and are chosen such that most of the light reaching the screen 406 from the microdischarge passes through the screen 406. The thickness of the screen 406 may range from 10 Å–10 mm, and preferably ranges from 1 μm–500 μm including 10 Å–10 μm, 10 Å–1 μm, and 100 Å–1 μm, dependent on the diameter of the channel 408. Other conductive materials may also be used to form a conducting electrode over the channel. Such materials include indium tin oxide (ITO), which does not absorb substantially in the visible.

Figure 10:
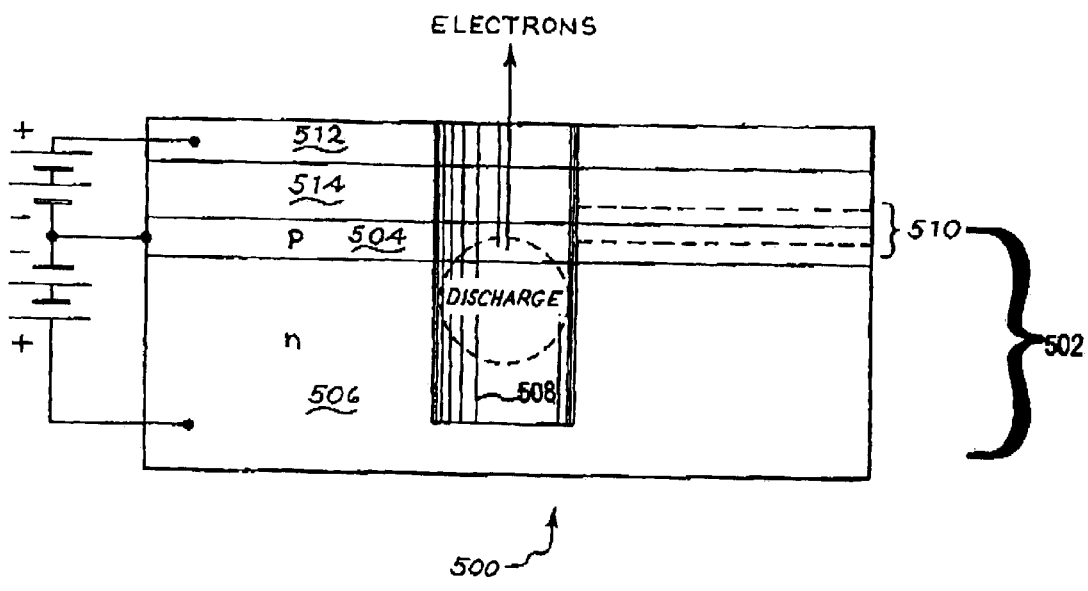
FIG. 10 is a cross-sectional view of an embodiment of the microdischarge device of the present invention.

In addition to light being emitted from the channel, electrons may also be extracted from the channel, thereby forming a plasma cathode. This effect is illustrated in another embodiment, shown in FIG. 10. The diode 502 forming the microdischarge device 500 has a p-type semiconductor layer 504, a n-type semiconductor layer 506 and a channel 508 similar to that of the first embodiment. In addition, however, an electrode 512 and dielectric layer 514 are disposed above the upper p-type layer 504, with the dielectric layer 514 sandwiched between the electrode 512 and the p-type layer 504.

The electrode 512 establishes a potential difference across the dielectric layer 514 that may be independent of that across the diode 502 (and depletion region 510). Thus, the electrode 512 is fabricated from a material that has good electrical and thermal conductivity. The electrode 512 may be planar and fabricated from one or more thin layers of conductive material, preferably having a thickness similar to that of the upper layer in the first embodiment. The electrode 512 is preferably thinner than the p-type layer 504. Common metals that may be used include copper, aluminum, gold, silver, nickel, and zinc and alloys thereof. Other conductors include polymers containing carbon black and other conducting polymer materials or highly doped crystalline, polycrystalline or amorphous semiconductor films such as Si. In addition, rather than the electrode 512 being formed from an optically opaque material, it may also be fabricated from a solid layer of an optically-transmissive material (at the wavelength of the discharge) such as ITO.

Similarly, the first electrode 512 may be fabricated from multiple layers, at least one of which (preferably the layer closest to the discharge) is electrically conducting. The other layers may serve act as a mirror to reflect light of undesired wavelengths back into the microdischarge. The electrode 512 is preferably deposited, plated, or otherwise disposed onto the dielectric layer 514 to establish a film of conducting material around the rim of the channel 508 in the dielectric layer 514.

The dielectric layer 514 is formed of a material with a resistivity of at least 0.1 Ω/cm, preferably from 0.5 Ω-cm–100 Ω-cm or from 1.0 Ω-cm–10.0 Ω-cm. The dielectric layer 514 acts as an insulator to electrically isolate the electrode 512 from the p-type layer 504. Preferably, the dielectric layer 514 has excellent thermostability and high dielectric strength, e.g. $T_g > 200°$ C. and at least $10^4$ V/cm, respectively. More preferable ranges for the thermostability include $400°$ C.$>T_g>250°$ C. and $350°$ C.$>T_g>275°$ C. and for the dielectric strength from $5\times10^4$ V/cm–$5\times10^6$ V/cm or $10^5$ V/cm–$5\times10^5$ V/cm. The dielectric layer 514 may be formed by growing, evaporating, spin coating, attaching with conductive paste or otherwise depositing a film onto the p-type layer 504.

The dielectric layer 514 may be formed from a polymer such as polyimide, which has exceptional thermostability and dielectric strength. For example, the breakdown voltage for a polyimide film about 5 µm thick is approximately 1.2 kV, giving a dielectric strength in excess of $10^6$ V/cm. Other dielectrics, resins and polymers—for example, oxide and nitride films such as $SiO_2$ or $Si_3N_4$, or KAPTON—may be used as long as the material retains its insulation properties at the material thickness required for adequate dielectric strength. In addition, multiple films of different materials (having at least one different dielectric constant) may be used to fabricate the dielectric layer 514 in order to improve both individual device and array performance. Measurements have shown that a multiple layer dielectric (containing, for example, ~0.5 µM $Si_3N_4$, 0.5 µm $SiO_2$, and several microns of polyimide) not only improves the voltage-current characteristics of an individual microdischarge device but also makes it possible to realize stable operation of large arrays (for example, 30×30) of devices. If, on the other hand, the dielectric layer 514 is a single film of polyimide, for example, it is difficult to operate arrays larger than approximately 5×5.

The dielectric layer 514, in addition to the electrode 512, may also be thin, preferably less than 100 µm. Preferred thickness ranges for the dielectric layer 514 may be from 10 Å–100 µm or 100 Å–10 µm. The voltage applied between the p-type layer 504 (or n-type layer 506) and the electrode 512 may extend the region of discharge or shape the flow of electrons. In either case, the electric field thus created is directly related to the thickness of the dielectric layer 514; as well as the particular gas and gas pressure in the channel 508. Scaling the thickness of the dielectric layer 514 thus changes the magnitude of the electric field in that region.

Although as depicted, the electrode 512 is a solid layer of conductive material, a screen (not shown) may be disposed on the electrode 512 or may serve as the electrode 512. Further, an electroluminescent material or phosphor may be disposed on the screen or onto a non-conducting window adjacent to the screen. In this case, electrons may be generated in the channel 508 by the voltage potential either in the depletion region 510 or in the dielectric layer 514. The majority of the electrons are then extracted from the channel 508 through the screen electrode and then impinge upon the phosphor, which luminesces.

Additionally, one variation on this embodiment would be to insert a non-conducting layer (not shown) between the screen and the electrode 512. This would allow one to operate the microdischarge continuously but illuminate the phosphor only when a voltage pulse is applied between the dielectric layer 514 and the screen that would attract the electrons towards screen. Alternatively, a conducting electrode that traverses the entire microdischarge device or array of microdischarge devices may replace the screen and present a uniform potential surface to the channel. An advantage of this embodiment is that the light output of the microdischarge device is not limited by the openness of the screen.

Figure 11:
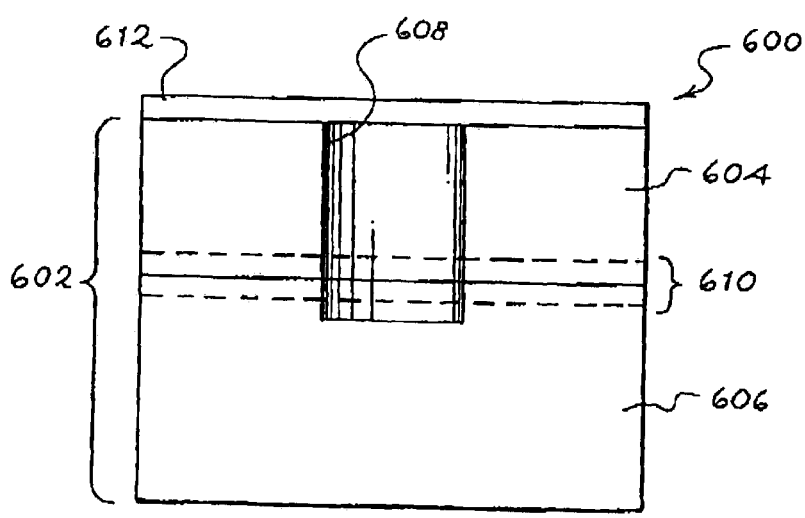
FIG. 11 is a cross-sectional view of an embodiment of the microdischarge device of the present invention.

In another embodiment, shown in FIG. 11, the microdischarge device 600 is similar to that of FIG. 2. In addition to the diode 602 having a p-type semiconductor layer 604, a n-type semiconductor layer 606 and a channel 608 formed through the depletion region 610, a sealing material 612 is added. The sealing material 612 is formed from an optically transmissive material and is preferably flexible. The optically transmissive material does not significantly absorb emissions from the device 600 at the wavelengths of operation.

A conventional plastic laminate, glass, quartz or mica may be used to seal the device 600. One problem with the plastic laminate is that the plastic outgasses impurities into the gas in the channel 608 and limits the lifetimes of laminated microdischarge device 600. However, the lifetime the gas is not a fundamental limitation on the device 600 lifetime. For example, the lifetime of the microdischarge device 600 will increase when using sealing materials that outgas less. Similarly, depositing (or otherwise disposing) a thin transmissive film such as tantalum oxide or glass onto conventional laminating sheets will impede or eliminate the outgassing process and extend the lifetime of the microdischarge device 600. Another alternative may be a vacuum baking procedure to significantly reduce the outgassing of conventional laminate sheets. As above, a screen and/or electrode/dielectric layer may be added to the basic structure before sealing. A phosphor/electroluminescent material may also be included on the screen before sealing.

The channel may be sealed while containing the desired gas at the proper pressure by laminating a plastic sheet on to one or both sides of the microdischarge device or array, thereby sealing the microdischarge device while still allowing the generated light to pass through the sealing material. Another method is to "hard seal" the devices to a quartz window having a conducting film or a fine metal grid on one side. The bonding process takes place with the conductor facing the electrode or lower semiconductor layer and bonding occurs along the entire perimeter thereof. When completed, this structure is robust and compact, requiring only electrical connections to an appropriate power supply or supplies.

One method of fabrication of the sealed microdischarge device having additional electrode and dielectric layers is to mechanically assemble the various layers on the substrate by individually positioning or forming the dielectric layer and electrode and/or screen on the substrate and subsequently forming the channel by etching or laser micromachining. Alternatively, the channel may be pre-formed in the various layers and then aligned during assembly. After the layers have been assembled and the channel formed, the channel may then be filled with a specified amount or pressure of a selected gas and then sealed while containing the desired gas at the proper pressure.

Figure 12A:
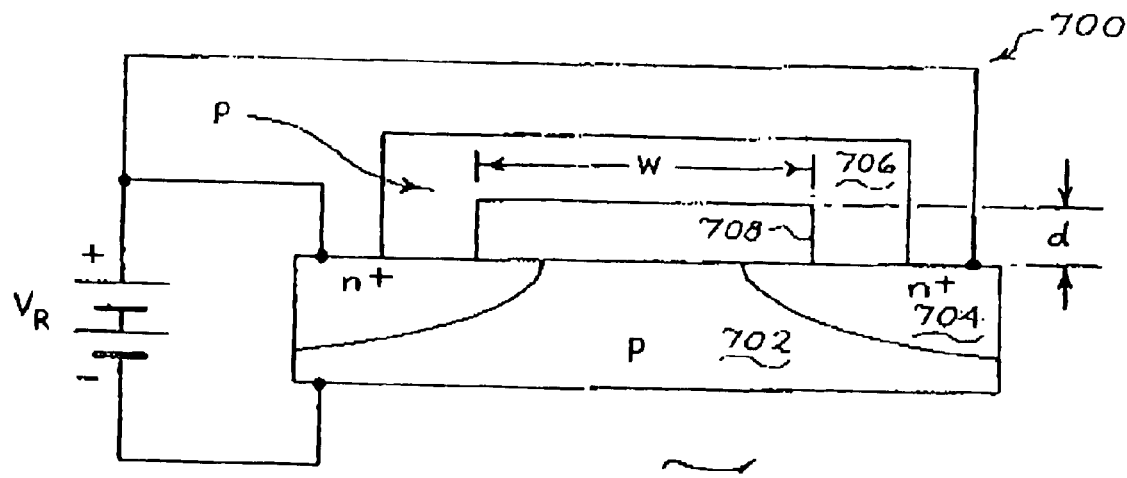
FIGS. 12a and 12b are cross-sectional and top views of a laser according to an embodiment of the microdischarge device of the present invention.
Figure 12B:
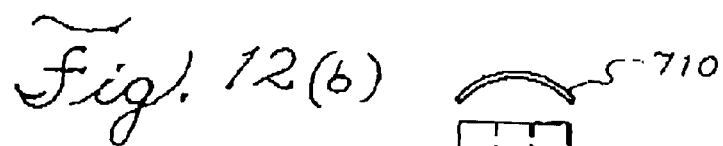

A laser 700 using microdischarge emission is illustrated in FIGS. 12a and 12b. FIG. 12a shows a cross-sectional view of a semiconductor laser structure having two Si wafers 702, 706. The lower wafer 702 is p-type with n⁺ regions 704 diffused into both sides. A rectangular channel 708 is micromachined into the upper, p-type wafer 706. The upper wafer 706 is in contact with and may be fused to the n⁺ regions 704. The channel 708 is filled with gas and serves as the channel of the laser 700. A reverse bias is applied between the p-type portion of the lower wafer 702 and the n⁺ regions 704, while either no voltage or an independent voltage is applied between the n⁺ regions 704 and the upper wafer 706. With the application of the proper reverse bias, a discharge is formed in the channel 708. As shown in FIG. 12b, this device 700 may be placed within a standard optical resonator having a pair of mirrors 710. The discharge light emitted from the ends of the channel 708 is coupled to the resonator and lasing can be obtained. These lasers can generate ultraviolet ($N_2$, rare gas halide excimers), visible, or infrared radiation that may be used in materials processing or atmospheric diagnostic applications.

Figure 13:
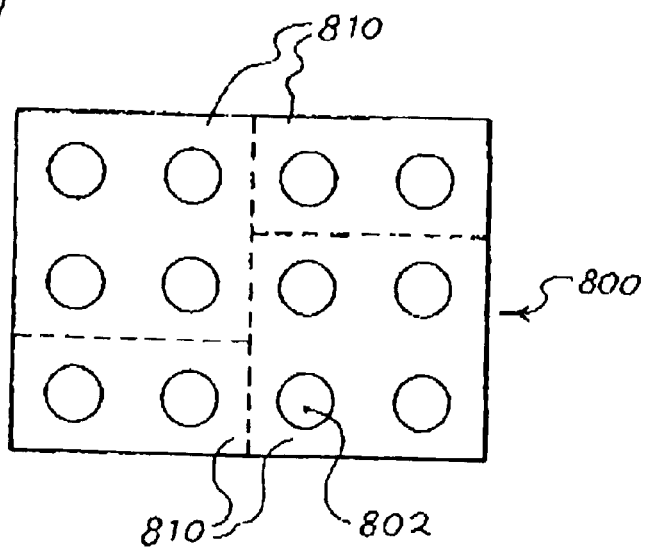
FIG. 13 is a top view of an array of an embodiment of the microdischarge devices of the present invention.

The above embodiments have focused on a single microdischarge device; however, as shown in FIG. 13, a plurality of microdischarge devices may be assembled into a planar array of devices 800. The individual devices 802 in the array 800 may be formed from any of the above embodiments.

A number of applications of microdischarge technology are accessible with these thin, low cost microdischarge arrays. Custom lighting and gas chromatography are examples of industrial applications that would be ideally suited for such a technology. To determine the composition of a gas, for example, the gas is allowed to flow laterally between a planar array of microdischarge devices and an opposing planar array of detectors. Each detector has an optical axis that coincides with the corresponding microdischarge device and has a filter that transmits a particular wavelength or set of wavelengths (i.e. a bandpass, low-pass or high-pass filter). Only particular wavelengths are transmitted by the gas, while others are absorbed. Thus, each detector detects light of a particular wavelength generated by the microdischarge devices and passing through the gas present. As the gas to be tested enters each microdischarge, it is energized (excited) and emits light at wavelengths characteristic of the particular gas components. Each detector, then, would observe a particular wavelength region, enabling the composition of the gas flow stream (or the presence of impurities in the gas flow stream) to be determined.

One method to determine the composition is to have the planar array emit light of a broad set of wavelengths and vary the filters of the corresponding detectors. Another method to determine the composition is to vary the wavelength of the light emitted from the microdischarge devices in the planar array, perhaps by varying the gas that fills the microdischarge devices, and having the same filter for each corresponding detector. In either case, data are collected and the composition of the gas determined from the transmission/absorption spectra of the gas. The microdischarge devices may emit either incoherent light (such as the custom lighting arrays above) or coherent light (as described by the lasers described below). Alternately, these methods may be combined—that is, various sets of microdischarge devices in the array could emit light of the same wavelength, with each set emitting light of a different wavelength from another set. In this case, various filters may be used to transmit light to the detectors.

In another application, the array of microdischarge devices may be used in the remediation of toxic gases. This application entails flowing a gas that is environmentally hazardous or toxic through the channels to break down the gas into benign products. Alternatively, the products of the gas discharge can be reacted with a titration gas ($O_2$, $N_2$, etc.) to produce a benign product rather than being completely broken down. In this application, the flow of the hazardous/toxic gas through the channel is imperative and thus, the microdischarge devices would not be sealed by a laminate. Note that in some applications, such as chemical sensors, only a few tens of individual devices may be required, while in other applications, such as industrial lighting, tens of thousands to millions of individual lighting may be required.

Ohmic losses become a problem if one wishes to fabricate large arrays of microdischarge devices. Large arrays often do not ignite uniformly; rather, devices at the perimeter of the array ignite preferentially. To overcome this problem, the overall array 800 may be divided into sub-arrays 810 and deliver power separately to the sub-arrays 810. The sub-arrays 810 may be independently excited such that they no longer ignite preferentially but in a desired arrangement. For example, while one voltage may be applied to a common substrate of the sub-arrays 810, different voltages may be applied to the upper semiconductor layer. Alternatively, the entire array may have multiple conductive leads from the voltage source and provided to selected areas of the array or may have continuous strips of the conductive leads crossing the array in a grid-like manner. Further, each device may be individually excited and ballasted. These arrangements are only examples of techniques that may be used to provide the desired uniformity to the array.

Such designs minimize ohmic losses in the electrodes as arrays increase in size and improve the characteristics and reproducibility for igniting the array or collection. In addition, these designs decrease the voltage variation appearing across individual devices in at least 10 of the devices in the array. This decrease is such that when a minimum voltage sufficient to cause discharging of the at least 10 of the devices is applied then the voltage difference between the first and second electrodes at every cavity of the discharge devices has a voltage difference of no more than 20% of the average voltage difference. The lower the voltage difference between a desired set of devices in the array, the better the uniformity in emission. Thus, more preferably the voltage difference may be no more than 10%, 5%, 2%, or 1% of the average voltage difference of at least 10, 20, 50, 100, 1000 or 10,000 devices.

In addition to exciting the sub-arrays independently, if an electrode and dielectric layer combination is present, using a multiple film dielectric as the dielectric layer allows one to realize much larger arrays that are well behaved. The addition of a screen on top of the electrode or replacing the electrode with a screen still further improves device and array characteristics, as discussed below.

While the invention has been described with reference to specific embodiments, the description is illustrative of the invention and not to be construed as limiting the invention. Various modifications and applications may occur to those skilled in the art without departing from the true spirit and scope of the invention as defined in the appended claims.

We claim:

1. A discharge device, comprising:
    a junction diode comprising at least a first layer serving as an anode of the discharge device under forward bias conditions, a second layer serving as a cathode of the discharge device under forward bias conditions, and a channel extending through a surface of at least one of the first and second layers; and a gas disposed within the channel wherein a discharge is formed when the diode is reversed-biased to excite the gas in the channel.

2. The discharge device of claim 1, wherein the first layer is a p-type semiconductor and the second layer is a n-type semiconductor.

3. The discharge device of claim 2, wherein the p-type semiconductor and the n-type semiconductor comprise the same semiconductor material with different majority dopants.

4. The discharge device of claim 1, further comprising a semiconductor layer disposed between the first and second layers, the semiconductor layer having a lower electrical conductivity than the first and second layers.

5. The discharge device of claim 1, wherein the first layer is a semiconductor and the second layer is a metal.

6. The discharge device of claim 1, further comprising a dielectric layer and an electrode layer, the first layer disposed between the second layer and the dielectric layer, the dielectric layer disposed between the first layer and the electrode layer.

7. The discharge device of claim 1, wherein the channel extends through the surface of the first layer and the first layer has an annular chamfer that widens the channel at the surface of the first layer and permits coupling to an optical fiber.

8. The discharge device of claim 1, further comprising an electrically conducting screen disposed on at least one of end of the channel.

9. The discharge device of claim 1, further comprising an optically transmissive sealing material to seal the channel, the sealing material not substantially absorbing light of a selected wavelength emitted by the gas when the gas is electrically excited.

10. An array of discharge devices according to claim 1.

11. The array of discharge devices of claim 10, wherein the array is divided into independently excited sub-arrays.

12. A lighting array comprising the array of discharge devices according to claim 11.

13. A laser comprising a plurality of the discharge devices according to claim 1.

14. The discharge device of claim 1, wherein at least one of the first layer and second layer comprises Si.

15. The discharge device of claim 1, wherein a junction is formed between the first and second layers, a depletion region is formed on at least one side of the junction, and the channel is formed in the depletion region.

16. The discharge device of claim 15, wherein the depletion region is formed on both sides of the junction.

17. The discharge device of claim 15, wherein the depletion region is formed on only one side of the junction.

18. The discharge device of claim 1, wherein the first layer physically contacts the second layer.

19. The discharge device of claim 1, wherein a depletion region is formed in at least one of the first and second layers and the channel is formed through at least a portion of the depletion such that a discharge is ignitable and sustainable in the portion of the channel corresponding to the depletion region when a reverse voltage is applied to the depletion region.

20. The discharge device of claim 1, further comprising electrodes in electrical contact with the first and second layers through which a reverse bias may be applied to the first and second layers.

21. The discharge device of claim 20, wherein no dielectric layer exists between the electrodes.

22. The discharge device of claim 1, wherein the device is configured such that a depletion region is generated in at least one of the first and second layers by an applied electric field, the channel is formed through at least a portion of the depletion region, and a width of the depletion region is variable, dependent on the applied electric field.

23. The discharge device of claim 1, wherein the device is configured such that a depletion region is generated in the diode by an applied electric field, the channel is formed through at least a portion of the depletion region, and a width of the depletion region is variable, dependent on the applied electric field.

24. A discharge device, comprising:
a semiconductor junction diode comprising at least a p-type semiconductor layer serving as an anode of the discharge device under forward bias conditions, an n-type semiconductor layer serving as a cathode of the discharge device under forward bias conditions, and a channel extending through a surface of at least one of the p-type semiconductor layer and n-type semiconductor layer; and
a gas disposed within the channel.

25. The discharge device of claim 24, further comprising an intermediate semiconductor layer disposed between the p-type semiconductor layer and n-type semiconductor layer, the intermediate semiconductor layer having a lower electrical conductivity than the p-type semiconductor and n-type semiconductor layers.

26. The discharge device of claim 24, further comprising a dielectric layer and an electrode layer, one of the p-type and n-type semiconductor layers disposed between the other of the p-type and n-type semiconductor layers and the dielectric layer, the dielectric layer disposed between the one of the p-type and n-type semiconductor layers and the electrode layer.

27. The discharge device of claim 24, wherein the one of the p-type and n-type semiconductor layers having the surface through which the channel extends comprises an annular chamfer that widens the channel at the surface and permits coupling to an optical fiber.

28. The discharge device of claim 24, further comprising a conducting screen disposed on at least one of end of the channel.

29. The discharge device of claim 24, further comprising an optically transmissive sealing material to seal the channel, the sealing material not substantially absorbing light of a selected wavelength emitted by the gas when the gas is electrically excited.

30. The discharge device of claim 24, wherein at least one of the p-type and n-type semiconductor layers comprises Si.

31. An array of discharge devices according to claim 24.

32. The array of discharge devices of claim 31, wherein the array is divided into independently excited sub-arrays.

33. A lighting array comprising the array of discharge devices according to claim 31.

34. A laser comprising a plurality of the discharge devices according to claim 24.

35. The discharge device of claim 24, wherein the channel extends through a depletion region of the diode.

36. The discharge device of claim 24, wherein the p-type semiconductor and the n-type semiconductor comprise the same semiconductor material with different majority dopants.

37. The discharge device of claim 24, wherein a depletion region is formed in the diode and the channel is formed in the depletion region in at least a portion of the depletion region such that a discharge is ignitable and sustainable in the portion of the channel corresponding to the depletion region when a reverse voltage is applied to the depletion region.

38. The discharge device of claim 24, wherein the p-type semiconductor layer contacts the n-type semiconductor layer.

39. The discharge device of claim 24, further comprising electrodes in electrical contact with the first and second layers through which a reverse bias may be applied to the first and second layers.

40. The discharge device of claim 39, wherein no dielectric layer exists between the electrodes.

41. A method of fabricating a discharge device, the method comprising forming a junction diode with a channel extending through a surface of the diode and establishing layers of the diode as an anode and a cathode of the discharge device wherein a discharge is formed by reverse biasing the diode to excite a gas in the channel.

42. The method of claim 41, further comprising forming the channel by one of mechanical drilling, ultrasonic drilling, optical drilling, wet chemical etching, and dry etching.

43. The method of claim 41, wherein the diode comprises a p-type and n-type semiconductor material and the method further comprises removing a portion of both the p-type and n-type semiconductor material to form the channel.

44. The method of claim 41, wherein the diode comprises at least one metal and semiconductor material and the method further comprises removing a portion of both the semiconductor material and metal to form the channel.

45. The method of claim 41, wherein the channel comprises an annular chamfer that widens the channel at the surface of the diode and the method further comprises coupling an optical fiber to the annular chamfer.

46. The method of claim 41, further comprising altering an electric field present in the channel by affixing a conducting screen to at least one of end of the channel.

47. The method of claim 41, further comprising sealing the channel with an optically transmissive sealing material that does not substantially absorb light of a selected wavelength emitted by the gas in the channel when the gas is electrically excited.

48. The method of claim 41, wherein the diode comprises at least one semiconductor layer and the method further comprises forming the at least one semiconductor layer of the diode by one of diffusing dopant into the semiconductor layer and growing the semiconductor layer on a base surface.

49. The method of claim 41, further comprising arranging a plurality of the devices in an array.

50. The method of claim 49, further comprising dividing the array into independently excited sub-arrays.

* * * * *